United States Patent [19]

Kaneyasu et al.

[11] Patent Number: 4,469,878
[45] Date of Patent: Sep. 4, 1984

[54] METHOD FOR MANUFACTURE OF PHTHALIC ANHYDRIDE

[75] Inventors: Masataka Kaneyasu; Tadanori Hara, both of Kitakyushu, Japan

[73] Assignee: Nippon Steel Chemical Co., Ltd., Tokyo, Japan

[21] Appl. No.: 424,636

[22] Filed: Sep. 27, 1982

[30] Foreign Application Priority Data

Sep. 30, 1981 [JP] Japan .................. 56-155657
Sep. 30, 1981 [JP] Japan .................. 56-155658

[51] Int. Cl.$^3$ ........................................... C07D 307/89
[52] U.S. Cl. ..................................... 549/248; 502/209
[58] Field of Search ........................................ 549/248

[56] References Cited

U.S. PATENT DOCUMENTS 4,046,780  9/1977  Nakanishi et al. ............... 549/248
4,324,694  4/1982  Reuter et al. .................... 549/248

FOREIGN PATENT DOCUMENTS 1553728  10/1979  United Kingdom .

*Primary Examiner*—Richard L. Raymond

*Attorney, Agent, or Firm*—Gordon W. Hueschen

[57] ABSTRACT

A method for the manufacture of phthalic anhydride by the catalytic oxidation of naphthelene or ortho-xylene which comprises contacting a mixed gas consisting of naphthalene or ortho-xylene and a molecular oxygen-containing gas with a catalyst bed comprising a first catalyst packed on the upstream side of the flow of mixed gas and a second catalyst packed on the downstream side of the flow, wherein the first catalyst has carried on a nonporous inactive carrier a catalytically active component composed of 67 to 90% by weight of titanium dioxide, 9 to 30% by weight of vanadium pentoxide and 0.7 to 3% by weight of a rubidium compound (calculated as $Rb_2SO_4$), and the second catalyst has carried on the nonporous inactive carrier a catalytically active component composed of 67 to 94% by weight of titanium dioxide, 5 to 30% by weight of vanadium pentoxide and at least one member selected from the group consisting of 0.1 to 1% by weight of a tin compound (calculated as $SnO_2$) and 0.5 to 3% by weight of a phosphorus compound (calculated as $SnO_2$).

12 Claims, No Drawings

4,469,878

METHOD FOR MANUFACTURE OF PHTHALIC ANHYDRIDE

BACKGROUND OF THE INVENTION

1. Field of the Invention

This invention relates to a method for the manufacture of phthalic anhydride. More particularly, this invention relates to a method for producing phthalic anhydride by subjecting naphthalene or ortho-xylene in a gaseous phase to catalytic oxidation with a molecular oxygen-containing gas.

2. Description of Prior Art

Phthalic anhydride, as widely known, is produced commercially by passing a mixed gas consisting of naphthalene or ortho-xylene and a molecular oxygen-containing gas at elevated temperatures through a shell-and tube reactor packed with a catalyst thereby causing catalytic oxidation of naphthalene or ortho-xylene. A typical catalyst usable for this method comprises a non-porous inactive carrier and a catalytically active substance comprising 1 to 15% be weight of vanadium pentoxide and 99 to 85% by weight of titanium dioxide deposited in a layer of a thickness of 0.02 to 2 mm on the carrier and used in an amount such that the vanadium pentoxide content falls in the range of 0.05 to 3% by weight based on the catalyst (U.S. Pat. No. 3,464,930). There has been proposed another method which has a phosphorus compound further included in the catalytically active substance deposited on the carrier in the aforementioned catalyst (U.S. Pat. No. 3,684,741). A typical catalyst to be used in this method comprises a nonporous inactive carrier and a catalytically active substance consisting of 1 to 40% by weight of vanadium pentoxide and 60 to 99% by weight of titanium dioxide and superposed in a thin layer on the aforementioned carrier, with the catalytically active substance further containing therein rubidium and/or cesium in the form of an oxide in an amount of 0.15 to 1.5% by weight based on the titanium dioxide and having a vanadium pentoxide content of 0.05 to 4% by weight based on the catalyst (German Offenlegungsschrift No. P 24 36 009).

Generally it is known that in a catalyst for the oxidation of naphthelene which has vanadium pentoxide and titanium dioxide as main catalytic components, an alkali metal compound added to the catalytic components prevents naphthalene from excessive oxidation and improved selectivity for phthalic anhydride or for phthalic anhydride and naphthoquinone. Since the alkali metal compound is added in a large amount, however, the catalytic activity is notably lowered and the yield is lowered. Thus, it has been customary to add this compound only in a small amount as in the methods of the aforementioned patents. Particularly in the case of rubidium, even when it is added in a small amount, it exhibits a notably high effect as compared with potassium and other alkali metals. Thus, it has been held not advantageous to add rubidium in a large amount.

Besides, the conventional methods such as described above have proved unsatisfactory in terms of repression of by-products, life of catalyst, yield of phthalic anhydride, etc. These problems become quite conspicuous when naphthalene is used as the raw material. These problems gain in seriousness in proportion as the concentration of naphthalene or ortho-xylene in the feed gas increases. Economically, however, it is desirable that the concentration of naphthalene or ortho-xylene should be so high as to exceed the lower explosive limit. In the meantime, the formation of by-products can be decreased by carrying out the oxidation at as high a temperature, at as low a gas feed volume (for as long a retention time), and in as low a concentration of naphthalene or ortho-xylene as possible. Under the conditions satisfying all these requirements, however, the productivity of phthalic anhydride is low.

With a view to eliminating the drawbacks mentioned above, there has been proposed a method for effecting the gaseous-phase oxidation of naphthalene or ortho-xylene by using on the up-stream side of the flow of a mixed gas of raw materials a first catalyst carrying thereon a catalytically active substance consisting of vanadium pentoxide and titanium dioxide and containing rubidium in an amount of 0.01 to 0.3% by weight based on the titanium dioxide and containing no phosphorus and on the downstream side of the flow a second catalyst carrying therein a catalytically active substance consisting of vanadium pentoxide and titanium dioxide and containing phosphorus in an amount of 0.02 0.8% by weight based on the titanium dioxide and containing no rubidium (German Offenlegungsschrift No. P 25 46 268). Even this method has a problem that the yield of phthalic anhydride is not sufficient as a whole. This problem is particularly conspicuous when naphthalene is used as the raw material.

It is, therefore, an object of this invention to provide an improved method for the manufacture of phthalic anhydride.

Another object of this invention is to provide a method for producing phthalic anhydride in high yield and with high productivity.

SUMMARY OF THE INVENTION

The objects described above are attained by a method for the manufacture of phthalic anhydride by the catalytic oxidation of naphthalene or ortho-xylene which comprises contacting a mixed gas consisting of naphthalene or ortho-xylene and a molecular oxygen-containing gas with a catalyst bed comprising a first catalyst packed on the upstream side of the aforementioned flow of mixed gas and a second catalyst packed on the downstream side of the flow, wherein the first catalyst has carried on a nonporous inactive carrier a catalytically active component composed of 67 to 90% by weight of titanium dioxide, 9 to 30% by weight of vanadium pentoxide and 0.7 to 3% by weight of a rubidium compound (calculated as $Rb_2SO_4$), and the second catalyst has carried on the nonporous inactive carrier a catalytically active component composed of 67 to 94% by weight of titanium dioxide, 5 to 30% by weight of vanadium pentoxide and at least one member selected from the group consisting of 0.1 to 1% by weight of a tin compound (calculated as $SnO_2$) and 0.5 to 3% by weight of a phosphorus compound (calculated as $P_2O_5$).

PREFERRED EMBODIMENT OF THE INVENTION

The first catalyst to be used as packed on the upstream side of the flow of the mixed gas of raw materials in the present invention is formed by having carried on a nonporous inactive carrier 20 to 200 g, preferably 40 to 150 g, per liter of the carrier of a catalytically active component composed of 67 to 90% be weight, preferably 70 to 85% by weight, of titanium dioxide, 9 to 30% by weight, preferably 15 to 25% by weight, of vanadium pentoxide, 0.7 to 3% by weight, preferably 1.0 to 2.0% by weight, of rubidium (calculated as $Rb_2SO_4$). The aforementioned catalytically active component substantially does not contain either a tin compound or a phosphorus compound. Optionally, it may contains compounds such as of K, Cs and Fe in small amounts. This catalyst may be produced by an ordinary method. For example, it may be produced by dissolving vanadium pentoxide or any of vanadium compounds such as, for example, ammonium vanadate, and sulfate, oxalate, formate, acetate and tartrate of vanadium which are converted by heating to vanadium pentoxide in water or a mixed solvent of an organic solvent such as alcohol with water, combining the resultant solution with a suitable rubidium compound and finely divided titanium dioxide, then, either spraying an inactive carrier with the resultant slurry-like mixture or immersing the inactive carrier in the slurry-like mixture, and heating the carrier with the slurry-like mixture, or spraying the slurry-like mixture on the carrier heated in advance to a stated temperature.

Examples of the rubidium compound advantageously usable herein include rubidium sulfate, rubidium oxide, rubidium carbonate, rubidium acetate and rubidium nitrate. Rubidium sulfate is preferred to the other rubidium compounds cited above. These rubidium compounds except rubidium sulfate are converted into their corresponding oxides at relatively high temperatures. In the catalyst, rubidium exists as rubidium sulfate, rubidium oxide or rubidium vanadate, for example. The most desirable form is the oxy-acid salt or sulfur such as rubidium sulfate or rubidium pyrosulfate.

The second catalyst to be used, as packed on the downstream side of the flow of the mixed gas of raw materials is formed by having carried on a nonporous inactive carrier 20 to 200 g, preferably 40 to 150 g, per liter of the aforementioned carrier of a catalytically active component composed of 67 to 94% by weight, preferably 70 to 85% by weight, of titanium dioxide, 9 to 30% by weight, preferably 15 to 25% by weight, of vanadium pentoxide, and 0.1 to 1% by weight, preferably 0.2 to 0.6% by weight, of a tin compound (calculated as $SnO_2$) and/or 0.5 to 3% by weight, preferably 1 to 2% by weight, of a phosphorus compound (calculated as $P_2O_5$). The aforementioned catalytically active component substantially does not contain an alkali metal compound such as a rubidium compound. Optionally, it may contain compounds of Fe, Cr, Mo and W in small amounts.

This catalyst may be produced by an ordinary method, for example. To be specific, it may be produced by dissolving vanadium pentoxide or any of the aforementioned vanadium compounds capable of being converted by heating into vanadium pentoxides in water or in the aforementioned organic solvent, combining the resultant solution with either or both of a suitable tin compound and a suitable phosphorus compound and with finely divided titanium dioxide, then either spraying an inactive carrier with the resultant slurry-like mixture or immersing the inactive carrier in the slurry-like mixture, and heating the carrier wet with the slurry-like mixture, or spraying the slurry-like mixture on the carrier heated in advance to a stated temperature.

Examples of the tin compound advantageously usable herein include tin oxide, stannic chloride and tin acetate. These tin compounds are converted into tin oxides when they are calcined. Examples of the phosphorus compound advantageously usable herein are ammonium phosphate, phosphoric acid, phosphorous acid and phosphoric esters.

The chemical names used in this specification to designate the components for the catalytically active substances are intended solely for the convenience of calculation. As is well known, actually in the catalyst, vanadium is present in the form of $VO_x$ ($x=1$ to 5) or a vanadate and rubidium in the form of rubidium sulfate or rubidium pyrosulfate, for example. By the same token, tin is present in the form of $SnO_x$ or a stannate and phosphorus in the form of $PO_x$ or a phosphate, for example.

Titanium dioxide in the form of anatase, titanium dioxide hydrate, etc. are available as sources for titanium oxide in the catalyst to be used in the present invention.

Examples of the nonporous inactive carrier to be used for the catalyst of the present invention are sintered or fused masses of silicates, steatite, ceramics, alumina and silicon carbide. To be effectively used in this invention, the aforementioned catalyst is desired to be in the shape of spheres, cylinders or rings, for example, which have an equivalent diameter of about 3 to 12 mm, preferably about 6 to 10 mm. The cylinders or rings of the catalyst have a height of about 3 to 10 mm, more desirably about 4 to 8 mm, and most desirably about 70 to 80% of the equivalent diameter. Among other shapes, the shape of rings proves desirable. Particularly the shape of Lessing rings which, as disclosed in Japanese Patent application Disclosure No. SHO 56(1981)-155,653, are a carrier of the shape of tubes each divided into two substantially equal cells by a partition wall disposed substantially perpendicularly to a plane in the diametric direction of the tube, with the tubes each measuring 6 to 10 mm in outside diameter, 4 to 8 mm in inside diameter, and 4 to 10 mm in height, the ratio of the thickness, b mm, of the partition wall to the thickness, a mm, of the peripheral wall of the tube, b/a, falling in the range of 0.4 to 0.8 (providing that b is larger than 0.5), and the thickness of the padding, C mm, of the peripheral wall at the joint between the peripheral wall and the partition wall and the length of the padding, d mm, in the circumferential direction from the intersection between the peripheral wall and the partition wall satisfying the formula, $C=e\times 0.1\sim 0.3-d\times 0.5\sim 1.5$ (providing that C is equal to or larger than 0 and e denotes the inside diameter in mm) proves particularly desirable because it suffers only a little pressure loss and permits oxidation in a high concentration. In the case of the carrier in the shape of rings, the inside diameter of each ring is 2 to 10 mm, preferably about 4 to 8 mm. In the case of the carrier in the shape of Lessing rings, it is proper that the rings should be provided with a partition wall substantially in the center and possessed of wall thickness of 0.5 to 2 mm, preferably 0.6 to 1 mm.

After the catalytically active substance has been deposited on the carrier, the resultant composite is heated to complete a catalyst. This heating is carried out at a temperature in the range of 300° to 600° C., preferably in an atmosphere of oxygen for a period of 4 to 10 hours to effect required thermal decomposition.

The catalyst completed as described above is used to pack a shell-and-tube reactor. Then, a mixed gas consisting of naphthalene or ortho-xylene and a molecular oxygen-containing gas such as air is passed through this reactor to effect catalytic oxidation of naphthalene or ortho-xylene. When the two catalysts are used as described above, the volumetric ratio of the first catalyst to the second catalyst generally is such that the second catalyst has a volume of 30 to 300 parts, preferably 30 to 150 parts, more preferably 30 to 95 parts, based on 100 parts of the first catalyst. Within the shell-and-tube reactor, the second catalyst is packed in a lower layer of a prescribed volume and the first catalyst is packed in an upper layer of a prescribed volume. Downwardly from the upper side of the reactor, the mixed gas consisting of naphthalene or ortho-xylene and a molecular oxygen-containing gas such as air is passed to effect the catalytic oxidation. The reaction temperature is 300° to 400° C., preferably 330° to 380° C., the concentration of naphthalene or ortho-xylene is 30 to 80 g/m³ of air, preferably 40 to 60 g/m³ of air, and the space velocity of the feed gas is 1,000 to 8,000 hr$^{-1}$, preferably 2,000 to 5,000 hr$^{-1}$.

In accordance with this invention, the selectivity of the conversion to phthalic anhydride is improved and the overall yield of phthalic anhydride is improved without entailing any notable drop of activity by suing the catalyst which incorporates rubidium in an amount of 0.7 to 3% by weight calculated as $Rb_2SO_4$. Owing to the use of the two catalysts described above, the first catalyst caused the oxidation with a relatively high selectivity to permit selective conversion of naphthalene or ortho-xylene to phthalic anhydride and the second catalyst effects the oxidation with a high activity and decreases the amount of untreated hydrocarbon to the fullest possible extent. As a whole, they permit phthalic anhydride to be obtained in a high yield, with the formation of by-produces decreased. The effect of the two catalysts is particularly conspicuous when naphthalene is used as the raw material.

Now this invention will be described more specifically below with reference to working examples. Whenever "%" is mentioned in the following working examples, it is meant to be % by weight unless otherwise specified.

EXAMPLES 1-22

(A) Preparation of first catalyst

Powdered titanium dioxide (containing anatase type titanium dioxide) was combined with an aqueous solution having ammonium metavanadate and rubidium sulfate dissolved in advance therein. The resultant mixture was thoroughly stirred and emulsified into a slurry liquid. In a rotary furnace, a ceramic carrier of the shape of Lessing rings having 8 mm of outer diameter, 5 mm of inner diameter, 6 mm of height and 1 mm of thickness of partition wall was placed and preheated therein to temperature of 200° to 250° C. Now with the rotary furnace kept in rotation, the preheated carrier was sprayed with the aforementioned slurry liquid so that the carrier would carry 80 g of the catalyst component per liter of carrier. Under a sweeping flow of air, the resultant composite was calcined at 550° C. for 6 hours to produce a catalyst.

The aforementioned treatments were so controlled that the catalytically active component of the produced catalyst would be composed of 18% of $V_2O_5$, 0.5 to 2.5% of $Rb_2SO_4$, and the balance to make up 100% of $TiO_2$.

(B) Preparation of second catalyst

Similarly to the first catalyst, powdered titanium dioxide, ammonium metavanadate, tin chloride or ammonium phosphate were added to deionized water. The resultant mixture was stirred and emulsified to produce a catalyst of the form of slurry liquid. By following the procedure used in the preparation of the first catalyst, this liquid catalyst was sprayed on a carrier of the shape of Lessing rings so that the carrier would carry 80 g of the catalyst component per liter of carrier. Under a sweeping flow of air, the resultant composite was calcined at 550° C. for 6 hours to produce a catalyst. The treatments mentioned above were so controlled that the catalytically active component of the produced catalyst would be composed of 20% of $V_2O_5$, 0.3 to 2.5% of $SnO_2$ or $P_2O_5$, and the balance to make up 100% of $TiO_2$.

(C) Production of phthalic anhydride

A reaction tube 25 mm in inside diameter immersed in niter bath was packed with a bed of the first catalyst and a bed of the second catalyst downwardly in the order mentioned. A mixed gas of naphthalene and air was passed through this reaction tube. The concentration of naphthalene was 50 g/Nm³, the space velocity was 3,000 hr$^{-1}$, and the temperature of niter was in the optimum range of 340° to 360° C. The results were as shown in Table 1.

TABLE 1

| Example No. | $Rb_2SO_4$ content of first catalyst (%) | $P_2O_5$ or $SnO_2$ content of second catalyst (%) | | Ratio of first to second catalyst bed in length | Yield of phthalic anhydride (%) | Yield of naphthoquinone (%) |
| --- | --- | --- | --- | --- | --- | --- |
| | | $P_2O_5$ | $SnO_2$ | | | |
| 1 | 2 | 1.5 | — | 3 | 104.0 | 2.5 |
| 2 | 2 | 1.5 | — | 1.8 | 104.7 | 0.8 |
| 3 | 2 | 1.5 | — | 1.1 | 104.5 | 0.03 |
| 4 | 2 | 2 | — | 1.8 | 104.6 | 0.4 |
| 5 | 2 | 2 | — | 1.1 | 103.7 | 0.2 |
| 6 | 1.5 | 2.5 | — | 1.1 | 102.6 | 0.02 |
| 7 | 1.5 | 2 | — | 1.8 | 104.0 | 0.2 |
| 8 | 1.5 | 2 | — | 1.1 | 103.8 | 0.06 |
| 9* | 1.5 | 2 | — | 1.1 | 103.6 | 0.25 |
| 10 | 1.5 | 1.5 | — | 1.1 | 103.7 | 0.03 |
| 11 | 1.5 | 1.5 | — | 1.8 | 103.9 | 0.21 |
| 12 | 1.0 | 2 | — | 1.1 | 103.0 | 0.01 |
| 13 | 3 | 1.5 | — | 3 | 103.1 | 1.3 |
| 14 | 0.7 | 2 | — | 1.1 | 101.0 | 0.01 |
| 15 | 2 | — | 0.5 | 1.1 | 102.5 | 0.02 |
| 16 | 2 | — | 0.5 | 1.8 | 103.2 | 0.2 |
| 17 | 2 | — | 0.3 | 3 | 103.6 | 1.7 |
| 18 | 2 | — | 0.3 | 1.8 | 104.7 | 0.8 |
| 19 | 2 | — | 0.3 | 1.1 | 103.5 | 0.3 |
| 20 | 1.5 | — | 0.3 | 3 | 103.9 | 0.9 |
| 21 | 1.5 | — | 0.3 | 1.8 | 104.1 | 0.7 |

TABLE 1-continued

| Example No. | $Rb_2SO_4$ content of first catalyst (%) | $P_2O_5$ or $SnO_2$ content of second catalyst (%) | | Ratio of first to second catalyst bed in length | Yield of phthalic anhydride (%) | Yield of naphthoquinone (%) |
|---|---|---|---|---|---|---|
| | | $P_2O_5$ | $SnO_2$ | | | |
| 22 | 1.5 | — | 0.3 | 1.1 | 103.2 | 0.2 |

*This Example shows datas after six month operation.

EXAMPLES 23-27

Catalysts were prepared by following the procedure of Example 1, except that the amount of $Rb_2SO_4$ in the preparation of the first catalyst and the amount of $P_2O_5$ or $SnO_2$ in the preparation of the second catalyst varied. The oxidation of naphthalene performed in Example 1 was repeated, except that the catalysts obtained herein were used instead. The results were as shown in Table 2.

TABLE 2

| Example No. | $Rb_2SO_4$ content of first catalyst (%) | $P_2O_5$ or $SnO_2$ content of second catalyst (%) | | Ratio of first to second catalyst bed in length | Yield of phthalic anhydride (%) | Yield of naphthoquinone (%) |
|---|---|---|---|---|---|---|
| | | $P_2O_5$ | $SnO_2$ | | | |
| 23 | 5 | 0 | 0 | 1.1 | 88.6 | 0.05 |
| 24 | 5 | 1.5 | 0 | 3 | 97.0 | 1.1 |
| 25* | 2 | — | | 1/0 | 94.9 | 8.2 |
| 26 | 5 | — | 1.0 | 3 | 93.9 | 0.3 |
| 27 | 0.2 | 1.5 | — | 1.1 | 85.0 | 0.01 |

*The reaction in this example used the first catalyst alone.

EXAMPLES 28-33

By following the procedure of Example 1, first catalysts and second catalysts were prepared and oxidation of naphthalene was performed by using these catalysts. In Examples 28-29 the content of $V_2O_5$ in the catalytically active component of the second catalyst was 10% and 30% respectively. In Examples 30-31, the concentration of naphthalene in the reaction conditions was 40 g/Nm$^3$ and 60 g/Nm$^3$ respectively. In Example 32, ceramics Rashig ring having 8 mm of outer diameter, 5 mm of inner diameter and 6 mm of height was used as the carrier in a similar procedure of Example 1. In Example 33, ortho-xylene was used as raw material instead of naphthalene and a temperature of niter was 380° C. in a similar procedure of Example 1. The results were shown in Table 3.

TABLE 3

| Example No. | $Rb_2SO_4$ content of first catalyst (%) | $P_2O_5$ content of second catalyst (%) | Ratio of first to second catalyst bed in length | Yield of phthalic anhydride (%) | Yield of naphthoquinone (%) |
|---|---|---|---|---|---|
| 28 | 2 | 1.5 | 1.1 | 103.5 | 0.03 |
| 29 | 2 | 1.5 | 1.1 | 104.4 | 1.7 |
| 30 | 2 | 1.5 | 1.1 | 102.7 | 0.01 |
| 31 | 2 | 1.5 | 1.1 | 104.4 | 0.30 |
| 32 | 2 | 1.5 | 1.1 | 102.5 | 0.01 |
| 33 | 1.5 | 2.0 | 1.1 | 114.4 | — |

What is claimed is:

1. A method for the manufacture of phthalic anhydride by the catalytic oxidation of naphthelene or ortho-xylene which comprises contacting a mixed gas consisting of naphthalene or ortho-xylene and a molecular oxygen-containing gas with a catalyst bed comprising a first catalyst packed on the upstream side of the flow of mixed gas and a second catalyst packed on the down-stream side of the flow, wherein the first catalyst has carried on a nonporous inactive carrier a catalytically active component composed of 67 to 90% by weight of titanium dioxide, 9 to 30% by weight of vanadium pentoxide and 0.7 to 3% by weight of a rubidium compound (calculated as $Rb_2SO_4$), and the second catalyst has carried on the nonporous inactive carrier a catalytically active component composed of 67 to 94% by weight of titanium dioxide, 5 to 30% by weight of vanadium pentoxide and at least one member selected from the group consisting of 0.1 to 1% by weight of a tin compound (calculated as $SnO_2$) and 0.5 to 3% by weight of a phosphorus compound (calculated as $P_2O_5$), said first catalytically active component substantially does not contain either a tin compound or a phosphorus compound and said second catalytically active component substantially does not contain an alkali metal compound whereby, in the upstream side, the mixed gas does not pass over a catalyst containing phosphorus.

2. A method according to claim 1, wherein said carrier is in the shape of masses.

3. A method according to claim 2, wherein said masses have an equivalent diameter of about 3 to 12 mm.

4. A method according to claim 2, wherein said masses are in the shape of rings.

5. A method according to claim 3, wherein said rings are Lessing rings have a height of 3 to 10 mm and the height is about 70 to 80% of the equivalent diameter of the rings.

6. A method according to claim 5, wherein said Lessing rings are tubes having an inside diameter of 2 to 10 mm, possessing a partition wall substantially in the center of the ring, and having a wall thickness of 0.5 to 2 mm.

7. A method according to claim 1, wherein said reaction is carried out at a temperature of 300° to 400° C. with the concentration of naphthalene or ortho-xylene in the range of 30 to 80 g/m$^3$ of air.

8. A method according to claim 1, wherein the volumetric ratio of the first catalyst to the second catalyst is such that the second catalyst has a volume of 30 to 300 parts based on 100 parts of the first catalyst.

9. A method according to claim 1, wherein the catalytically active component of the first catalyst is composed of 70 to 85% by weight of titanium dioxide, 15 to 25% by weight of vanadium pentoxide, and 1.0 to 2.0% by weight of rubidium compound (calculated as $Rb_2SO_4$) and the catalytically active component of the second catalyst is composed of 70 to 85% by weight of titanium dioxide, 15 to 25% by weight of vanadium pentoxide, and at least one member selected from the group consisting of 0.2 to 0.6% by weight of a tin compound (calculated as $SnO_2$) and 1 to 2% by weight of phosphorus compound (calculated as $P_2O_5$).

10. A method according to claim 9, wherein the volumetric ratio of the first catalyst to the second catalyst is such that the second catalyst has a volume of 30 to 90 parts based on 100 parts of the first catalyst.

11. A method according to claim 7, wherein said rubidium compound is rubidium sulfate.

12. A method according to claim 1, wherein said rubidium compound is rubidium sulfate.

* * * * *